United States Patent [19]

Naydich

[11] Patent Number: 4,807,651
[45] Date of Patent: Feb. 28, 1989

[54] DENTAL DEBRIS REMOVER

[76] Inventor: Abram Naydich, 7242 Wilbur Ave., Reseda, Calif. 91335

[21] Appl. No.: 812,283

[22] Filed: Dec. 23, 1985

[51] Int. Cl.⁴ .............................................. A61C 15/00
[52] U.S. Cl. ....................................................... 132/323
[58] Field of Search .............. 132/89, 91, 92 R, 92 A, 132/93

[56] References Cited

U.S. PATENT DOCUMENTS

| | | | |
|---|---|---|---|
| 272,985 | 2/1883 | Stone | 132/93 |
| 1,279,026 | 9/1918 | Sievers | 132/92 A |
| 2,873,749 | 2/1959 | Gjerde | 132/91 |
| 3,631,869 | 1/1972 | Espinosa | 132/91 |
| 3,746,017 | 7/1973 | Casselman | 132/92 A |
| 3,802,445 | 9/1972 | Wesley | 132/89 |
| 3,905,113 | 2/1974 | Jacob | 128/62 A |
| 4,011,658 | 3/1977 | Tarrson | 433/216 |
| 4,215,478 | 8/1980 | Thomas | 433/25 |
| 4,460,002 | 6/1984 | Burdette | 132/91 |
| 4,531,530 | 7/1985 | Aiken | 132/93 |

FOREIGN PATENT DOCUMENTS 0105654  4/1984  European Pat. Off. .............. 132/89

Primary Examiner—Gene Mancene
Assistant Examiner—Adriene Lepiane

[57] ABSTRACT

The dental debris remover includes a rigid sickle-shaped frame, a puller and a floss string member. The floss string member is formed in an endless loop to create a variety of configurations for more effective cleaning and to achieve quick attachment to the frame handle notches on one side and to the puller hooks on the other side. The end of the frame bending towards the handle has a soft hygienic external layer or coating. The device is designed to perform two main functions, between the teeth cleaning and under fixed denture cleaning.

1 Claim, 3 Drawing Sheets

DENTAL DEBRIS REMOVER

BACKGROUND OF INVENTION

1. Field of Invention

This invention relates to an article for oral hygiene and pertains particularly to dental surface cleaning devices. Further, this invention pertains to the class of disposable dental floss holding devices. More in particular, this invention pertains to the subclass of the dental cleaning devices which combine in one unit both means for cleaning dental surfaces between teeth and under dental fixed bridges or similar unremovable dentures.

The said combined feature is important for users with dental fixed bridges.

The device is designed to perform a dental cleaning process by users and to achieve several objectives which overcome deficiencies of previous art, namely:

combining in one reusable unit means for cleaning between teeth and under dental fixed bridges;

increasing efficiency of cleaning by employing different floss string member configurations;

simplifying dental floss string member insertion under dental fixed bridges and improving hygienic conditions at the same time;

providing the ability to adjust the tension of the dental floss string member during the cleaning procedure;

simplifying dental floss string member attachment;

preventing gum tissue damage from the rigid frame during device application;

providing suitability for mass production, preferably from plastic.

2. Prior Art

Different hygiene floss systems are well-known in the art and designed for use in cleaning and therapeutic functions. Medical prerequisites for the design of dental cleaning systems are known in the art and are described in detail in U.S. Pat. No. 3,905,113.

The closest prior inventions known to applicant include devices, methods, and cleaning systems disclosed in U.S. Pat. Nos. 4,011,658, 4,531,530, 4,215,478, and 4,460,002. These patents represent different classes of dental cleaning devices. The first two patents mentioned above pertain to devices or means and methods of usage for cleaning under dental fixed bridges or similar dentures.

Inconvenience of those systems of cleaning results when it is necessary to use two hands to perform the cleaning process. Another deficiency in the prior methods is the considerable amount of floss material required to hold the string itself.

An unhygienic aspect of the prior art cleaning procedures is the necessity to use a finger in the mouth area during cleaning.

The other two cleaning devices mentioned above are designed to perform cleaning exclusively between teeth.

U.S. Pat. No. 4,531,530 discloses a more effective method of cleaning by scrubbing the tooth surface with a tensioned string member. The support member for string attachment and tensioning is used at the same time as a cam slides along the edge of the tooth. This feature can be unacceptable for users with sensitive teeth. All above mentioned deficiencies of the prior patents are eliminated in the instant invention which includes several additional useful features stated above in the description of the objectives and disclosed below in the description of the invention.

BRIEF DESCRIPTION OF THE INVENTION

The dental debris remover of the instant invention comprises a rigid frame, a puller, and a floss string member.

The frame contains a handle, a fixing arm, a guide and has a substantially sicklewise shape with one end prebended opposite to where the said handle is secured. The handle contains a hole for receiving a finger and a lug with notches for string member attachment. The fixing arm, like the said handle and guide, is an integral part of the frame and is formed as a consol with back spring effect. It contains a slot with stopping teeth to fix the puller in appropriate position to achieve desirable string member tension. The puller is formed like a flexible thin sliding strip with one end prebended in a semicircle and containing hooks for string member attachment. The other of its ends is formed like a handle secured on the top of the driving and locking pin which contains two teeth matching the teeth of the said fixing arm. The puller is placed in the said frame guide from the frame handle side and has a limited movement towards the prebended frame end and back.

The floss string member is formed in an endless loop to create a variety of configurations for more effective cleaning and to simplify and achieve quick attachment to the frame handle notches on one side and to the puller hooks on the other side. The frame guide is used to direct the prebended end of the puller under dental fixed bridges within the user's inner mouth area.

The device is designed to perform two main functions: between teeth cleaning and under fixed denture cleaning. For between teeth cleaning the string member shall be initially attached to the said notches on the frame handle and to the hooks on the said puller. For this purpose the puller handle shall be moved towards the prebended frame end until a sufficient portion of the puller end will appear outside of the frame. After attachment to the string member the puller shall be moved back to tighten the string member and fix the puller. After this procedure the device is ready for between teeth insertion and cleaning.

To use the device for under fixed bridges cleaning the user shall direct the prebended end of the frame near the fixed denture in the inner area of the mouth and insert the puller end into the gap between the gum and said denture until a sufficient portion of the puller end appears outside the denture to attach the other side of the string member. After tightening, the cleaning procedure can be performed.

The choice of the string member configuration shall be made by the user and depends on both the kind of cleaning process (between teeth or under fixed denture) desired and the dimensions of the gaps between the teeth or between the gum and denture.

A variety of possible floss string member configurations will be disclosed later. The more complicated configuration shall provide more efficient cleaning because of the ability to better remove the debris.

Implementing the cleaning process comprises oscillating the said debris remover with the inserted and tightened floss string member back and forth, up and down, or in any effective direction.

BRIEF DESCRIPTION OF THE DRAWINGS

Reference numerals on the figures of the drawings indicate the corresponding elements given in the description.

Figure 1:
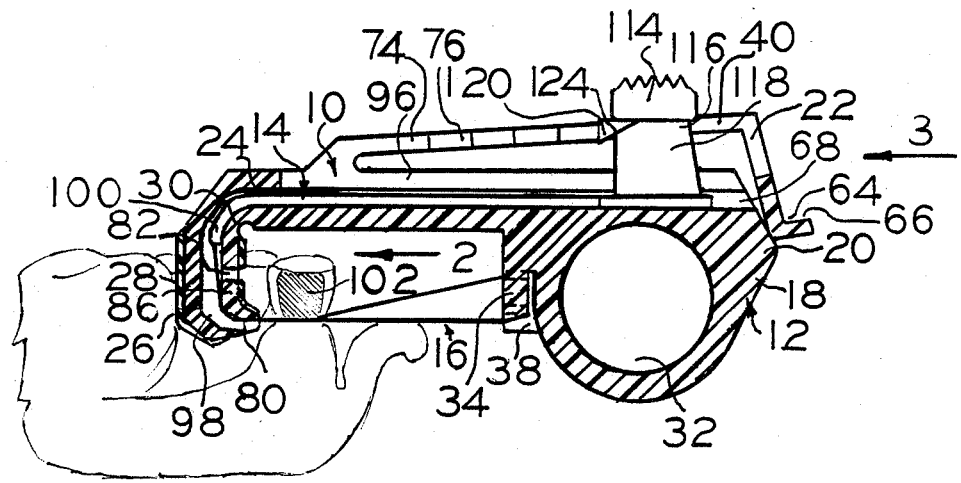
FIG. 1 is a longitudinal section of the dental debris remover.
Figure 2:
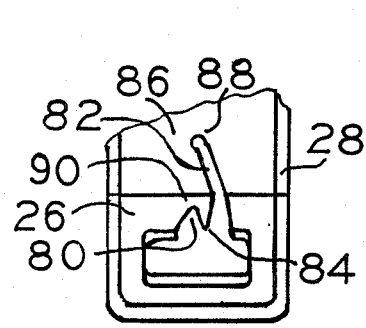
FIG. 2 is an enlarged fragmentary view of the frame bended end wall indicated by the arrowhead 2.
Figure 3:
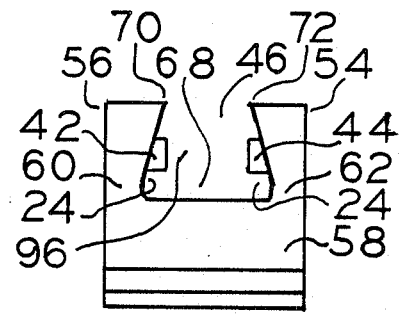
FIG. 3 is an enlarged fragmentary view of the frame guide opening indicated by arrowhead 3.
Figure 4:
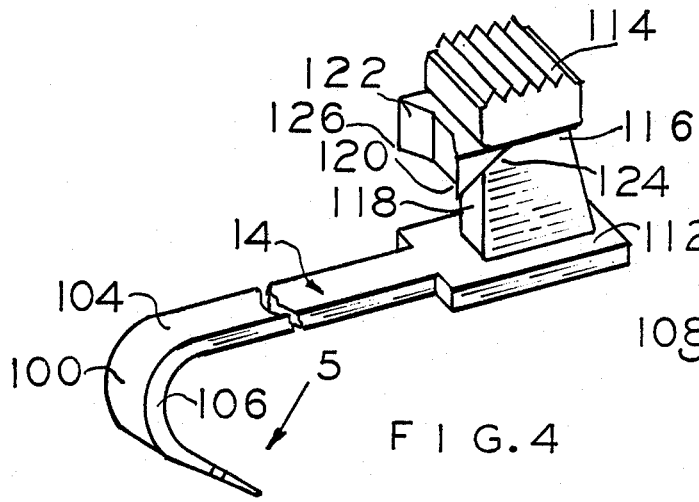
FIG. 4 is an enlarged perspective view of the puller.
Figure 5:
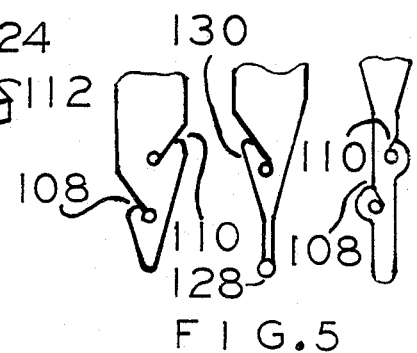
FIG. 5 illustrates some of the possible forms of the puller end with hooks indicated by arrowhead 5.
Figure 6:
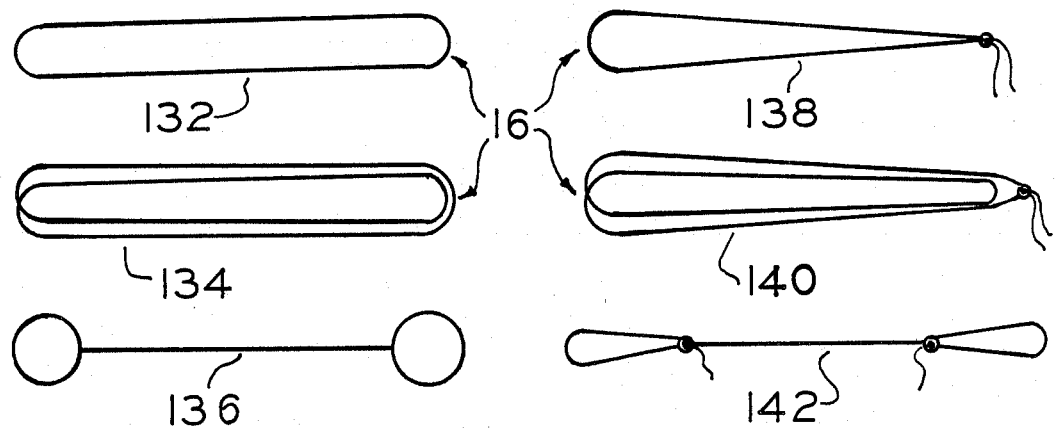
FIG. 6 illustrates some of the possible modifications of the endless loop floss string member.
Figure 7:
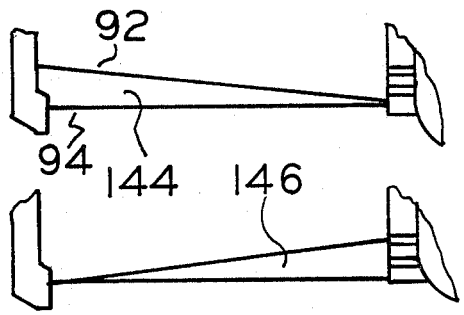
FIG. 7 illustrates two cases for the floss string member attachment: triangles in the vertical plane.
Figure 8:
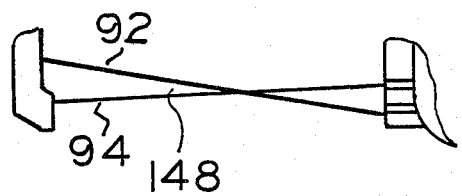
FIG. 8 illustrates the "X" configuration for the floss string member.
Figure 9:
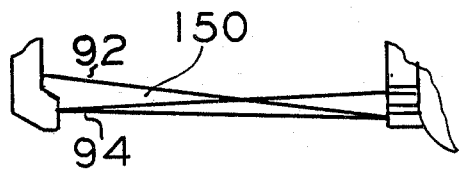
FIG. 9 illustrates the "X" configuration with the double floss string member branch in the low position.
Figure 10:
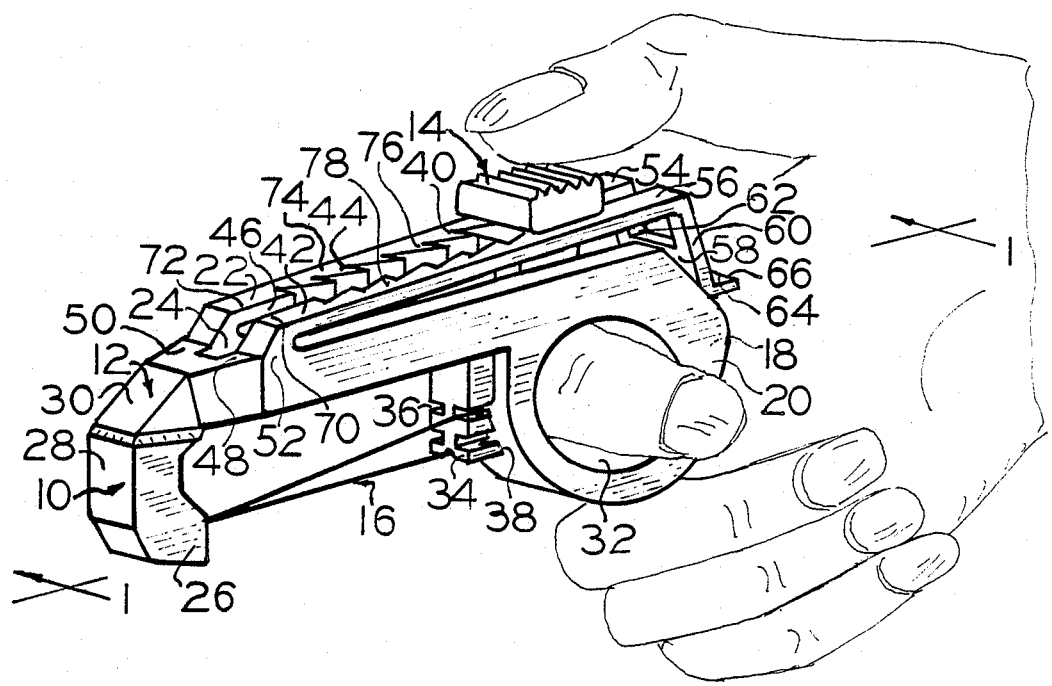
FIG. 10 is a perspective view of the dental debris remover.

The exemplifications set out herein illustrate a preferred embodiment of the invention in one form or with limited variations of some elements and such exemplifications are not to be understood as limiting the scope of the disclosure or the scope of the invention in any manner.

DETAILED DESCRIPTION OF THE INVENTION

Refering now to the drawings, the numeral 10 designates the dental debris remover which comprises a frame 12, a puller 14, and a floss string member 16.

The frame 12 includes a handle 18 on one end 20, a fixing arm 22, and a guide 24.

The other end 26 of the frame 12 is bended towards the handle 18 and contains a soft hygienic external layer or coating 28 which can be made from the original frame 12 material or another type of plastic or rubber. The frame bended end 26 provides in linkage area 30 some degree of flexibility with spring effect to implement approximately constant string member tension and positioning fixation of the puller 14.

The frame 12 with the handle 18, fixing arm 22, and guide 24 can be an integral structure as shown on the drawings. In simplifying the manufacturing process the fixing arm 22 can be produced separately and then attached to the frame 12.

The handle 18 contains a hole 32 for finger insertion and a lug 34. The lug 34 contains four notches 36 connected by open slot 38 to allow for string member 16 attachment.

The fixing arm 22 is formed like consol 40 with back spring effect and is divided into two parallel strip-like portions 42 and 44 by slot 46. Each portion is secured on an appropriate side 48 and 50 of the guide 24 in the midpoint 52 of the frame 12. The opposite sides 54 and 56 of the fixing arm parallel strips 42 and 44 are bended and contain an integral linkage 58 between their ends 60 and 62. The bended portions 54 and 56 with linkage 58 are used to create additional spring effect.

The linkage 58 is formed as a right angle 64 to create a surface 66 for pushing fixing arm 22 down to release puller 14. The linkage 58 must be positioned below the guide opening 68 in the frame 12 so as to allow the puller 14 to be inserted in the guide 24 when fixing arm 22 is pushed down. Each edge 70 and 72 of the slot 46 in their middle portion 74 contains symmetrical stop teeth 76 and 78 which are used to fix puller 14 in any position between adjacent teeth when fixing arm 22 is released.

The frame bended end 26 contains two notches 80 and 82 and separator 84 in its wall 86 to achieve two different levels 88 and 90 for string member 16 branches 92 and 94 during tightening.

The guide 24 has the same shape as the frame 12 in side view. A portion 96 of the guide 24 located under fixing arm 22 is open and has approximately "C" shape in cross section. The portion 96 is narrow in the end 26 area to provide guiding for the puller 14 in fixing arm 22 area. The portion 98 of the guide 24 is intended for directing and conducting the puller 14 end 100 under the fixed denture 102.

The puller 14 is formed like a flexible thin sliding strip 104 with one end 100 prebended in a semicircle 106 and contains two hooks 108 and 110 for string member 16 attachment. The other end 112 is formed like a handle 114 secured on the top 116 of the driving and locking pin 118 which contains two teeth 120 and 122 matching the teeth 76 and 78 of the fixing arm 22. The two cams 124 and 126 push the fixing arm 22 down during the tightening process. For some applications where a very narrow puller end 128 is required the puller 14 may have only one hook 130.

The floss string member 16 is formed in an endless loop which can be premanufactured or can be prepared by users himself or herself. There are three main modifications of the floss string member: the single loop 132, the double loop 134, and the single strip 136. The numerals 138, 140, and 142 demonstrate hand-made string members. The single string member is known in the art and disclosed in U.S. Pat. No. 3,802,445, but the said string member is assigned to use with the fingers and therefore requires a significant amount of floss material.

There are several possible distinctive configurations. The simplest one is demonstrated by numeral 136. The single or double loops (132, 134) can be used to create the following configurations:

two snug parallel strings;
four snug parallel strings;
two strings slightly separated in the vertical direction;
two strings slightly separated in the horizontal direction;
two snug strings slightly separated from two others in the vertical or horizontal directions
single or double string triangles, 144 and 146, in the horizontal or vertical directions;
single or double string "X"-configuration 148 in the vertical direction;
other configurations can be achieved by employing two separate string loops like that shown for instance by numeral 150.

It is important to note that the small distance between the parallel strings creates a compartment for the removal of debris.

What is claimed is:

1. A hygiene tool employing an endless loop floss member for debris removal between teeth and under fixed dentures or bridges comprising a floss puller and a sickle shaped frame, said frame including as integral parts a handle, a bended end, a guide, and a fixing arm, all lying in a same plane, said handle located at one end of said frame and having a circular opening formed by a ring integrated with said frame; disposed adjacent to said handle is a vertical projection having an inner surface and an outer surface, said inner surface facing said handle and having a convex surface, said vertical projection including four inwardly directed horizontal notches symmetrically arranged in two levels on either side of said vertical projection; said bended end having an external surface with a soft layer of hygenic material disposed opposite said vertical projection on another end of said frame, said bended end having a C-shaped configuration approximately rectangular in cross section and directed toward said vertical projection, said bended end having an inner wall and an outer wall, said inner wall facing said vertical projection and having two notches and a separator disposed between said two notches, said two notches each having a V-shaped opening at one end and another end located along a vertical center line of said inner wall, said other end of each of said two notches being disposed at different heights along said vertical center line for positioning said floss member at two different levels during tightening; said separator formed by one side of each of said V-shaped openings of said two notches allowing separation of said floss member during tightening; said guide having one end formed like a trough extending horizontally above said handle, said trough having an opening in the end of said frame located above said handle, said guide having another end opposite said opening where said trough ends in a track oriented between said inner wall and said outer wall of said bended end, said inner wall and said outer wall having walls extending therebetween to enclose said track, and said track at said bended end terminating in an opening facing said vertical projection; said fixing arm formed of two strips extending above said trough and said handle and separated from each other by means of a slot lying above and in the same plane with said trough, said two strips each having an inner side on which symmetrical, inwardly directed stop teeth are arranged, each of said inner sides defining one side of said slot; said two strips merging with said frame to form an acute angle close to said bended end and opposite said bended end, above the end of the frame, a toothless portion of said fixing arm extends at an angle directed downward and outward from said handle defining a linkage, said linkage in combination with said two strips providing a spring effect; said puller slidable along said guide is formed of a flexible, thin strip having one end prebended in a semicircular shape, said end having two hooks placed on different levels on opposite sides of said end, said two hooks each having a Y-shaped notch with an inner circular opening at a lower portion of said Y-shaped notch, said Y-shaped notch enabling said floss member to be easily threaded through said two hooks; said puller having a pin which functions as a driving and a locking means for said puller, said pin having a puller handle secured on top of said pin and two edges placed underneath said pin to provide a guiding surface as said puller slides through said guide, said pin having two puller teeth mounted thereon, said two puller teeth are located immediately under said puller handle, oriented toward said prebended end and adapted to engage said stop teeth; immediately behind said puller teeth are two cams each having a sloped surface enabling said puller to be released from said stop teeth.

* * * * *